US008845588B2

(12) United States Patent
Bruszewski

(10) Patent No.: US 8,845,588 B2
(45) Date of Patent: Sep. 30, 2014

(54) SHEATH INTRODUCER SYSTEM WITH EXCHANGEABLE HEMOSTATIC VALVES

(75) Inventor: Walter Bruszewski, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 407 days.

(21) Appl. No.: 13/089,592

(22) Filed: Apr. 19, 2011

(65) Prior Publication Data

US 2012/0271236 A1    Oct. 25, 2012

(51) Int. Cl.
*A61M 5/178* (2006.01)
*A61M 39/06* (2006.01)

(52) U.S. Cl.
CPC .... *A61M 39/0613* (2013.01); *A61M 2039/0633* (2013.01); *A61M 2039/0686* (2013.01); *A61M 39/0606* (2013.01); *A61M 2039/0673* (2013.01)
USPC .................................................. 604/167.03

(58) Field of Classification Search
CPC .................. A61B 17/3462; A61M 2039/0633; A61M 2039/064; A61M 2039/0653; A61M 25/0606
USPC .............. 604/167.01–167.06, 164.07–164.08
See application file for complete search history.

(56) References Cited

U.S. PATENT DOCUMENTS

| | | | |
|---|---|---|---|
| 5,125,903 A | 6/1992 | McLaughlin et al. | |
| 5,273,546 A | 12/1993 | McLaughlin et al. | |
| 6,213,988 B1 | 4/2001 | McIvor et al. | |
| 6,659,981 B2 | 12/2003 | Stewart et al. | |
| 6,743,227 B2 | 6/2004 | Seraj et al. | |
| 6,786,918 B1 | 9/2004 | Krivoruchko et al. | |
| 7,018,400 B2 | 3/2006 | Lashinski et al. | |
| 7,081,106 B1 * | 7/2006 | Guo et al. | 604/167.06 |
| 7,207,981 B2 | 4/2007 | Quinn et al. | |
| 7,356,903 B2 | 4/2008 | Krivoruchko et al. | |
| 7,582,070 B2 * | 9/2009 | Goode et al. | 604/167.04 |
| 7,591,832 B2 | 9/2009 | Eversull et al. | |
| 7,713,281 B2 | 5/2010 | Leeflang et al. | |
| 2002/0007152 A1 * | 1/2002 | Hermann et al. | 604/167.04 |
| 2003/0050604 A1 * | 3/2003 | Lui et al. | 604/167.06 |
| 2010/0094227 A1 * | 4/2010 | Albrecht et al. | 604/167.01 |

FOREIGN PATENT DOCUMENTS

WO    WO 03/039625 A2    5/2003

* cited by examiner

*Primary Examiner* — Nicholas Lucchesi
*Assistant Examiner* — Melissa A Snyder

(57) ABSTRACT

A sheath introducer system with exchangeable hemostatic valve modules is disclosed. A first valve module includes a single entry port to ensure hemostasis during the introduction of an interventional device, such as a main graft delivery system for treatment of an abdominal aortic aneurysm (AAA). A second valve module includes multiple entry ports to ensure hemostasis during the simultaneous introduction and manipulation of multiple interventional devices, such as multiple guiding catheters for use in delivering various intravascular graft components for completion of branch perfusion, for instance, during treatment of the AAA.

14 Claims, 6 Drawing Sheets

SHEATH INTRODUCER SYSTEM WITH EXCHANGEABLE HEMOSTATIC VALVES

FIELD OF THE INVENTION

The invention relates to a sheath introducer assembly for enlarging and maintaining a percutaneous opening in an arterial or venous vessel for providing a pathway for the introduction of interventional devices. More particularly, the invention is directed to a sheath introducer having exchangeable hemostatic valves wherein one of the valves ensures hemostasis during the simultaneous introduction and manipulation of multiple medical devices.

BACKGROUND OF THE INVENTION

The introduction of interventional devices into a given arterial or venous vessel for a variety of purposes, such as for performing percutaneous transluminal coronary angioplasty (PTCA) or for delivering and implanting a stent or stent graft, is well known in the art. Several techniques for introducing such catheters are available, including the Seldinger technique. Broadly described the Seldinger technique involves surgically opening a vein or artery with a needle, inserting a guidewire into the vein or artery through the lumen of the needle, withdrawing the needle, inserting over the guidewire a dilator located inside an associated sheath introducer having a hemostasis valve, removing the dilator and inserting a catheter through the hemostasis valve and sheath into the blood vessel. During this process, care must be exercised to prevent introduction of air into the vessel and to avoid leakage of blood from a proximal end of the sheath introducer. To avoid the risk of both air embolism and blood contamination of the clinician conventional introducers employ various types of hemostasis valves having a single proximal input port that is designed for use with catheters and guidewires that have various diameters.

In interventional procedures where it may be necessary to simultaneously utilize multiple interventional devices, such as procedures for percutaneously delivering and implanting endovascular grafts for treatment of certain types of abdominal aortic aneurysms, a sheath introducer with a hemostasis valve having a single proximal input port may not ensure hemostasis of each interventional device in use during the procedure. In such cases, a clinician may utilize a puncturable hemostasis valve that can be adapted to achieve modest hemostasis of multiple devices introduced through multiple punctures or alternatively modify a hemostasis valve known in the art by puncturing additional openings to introduce additional device(s), although hemostasis is generally very poor with this practice. As such a need exists in the art for a sheath introducer that ensures hemostasis during treatments that require the simultaneous introduction and manipulation of multiple catheters or other interventional devices.

BRIEF SUMMARY OF THE INVENTION

Embodiments hereof are directed to a sheath introducer system with exchangeable hemostatic valve modules. A first valve module includes a single entry port to ensure hemostasis during the introduction of an interventional device therethrough. A second valve module includes a plurality of entry ports to ensure hemostasis during the simultaneous introduction and manipulation of multiple interventional devices. The sheath introducer system includes a sheath introducer defining a lumen therethrough that has a proximal valve housing in fluid communication with a distal tubular sheath. An exchangeable valve module is coupled to the valve housing, wherein the valve module may be one of the first and second valve modules described above. A locking collar is provided for releasably securing the valve module to the sheath introducer valve housing. A side access slit may be provided to connect an entry port of the valve module with a periphery of the valve module to permit transverse introduction or removal of an interventional device.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
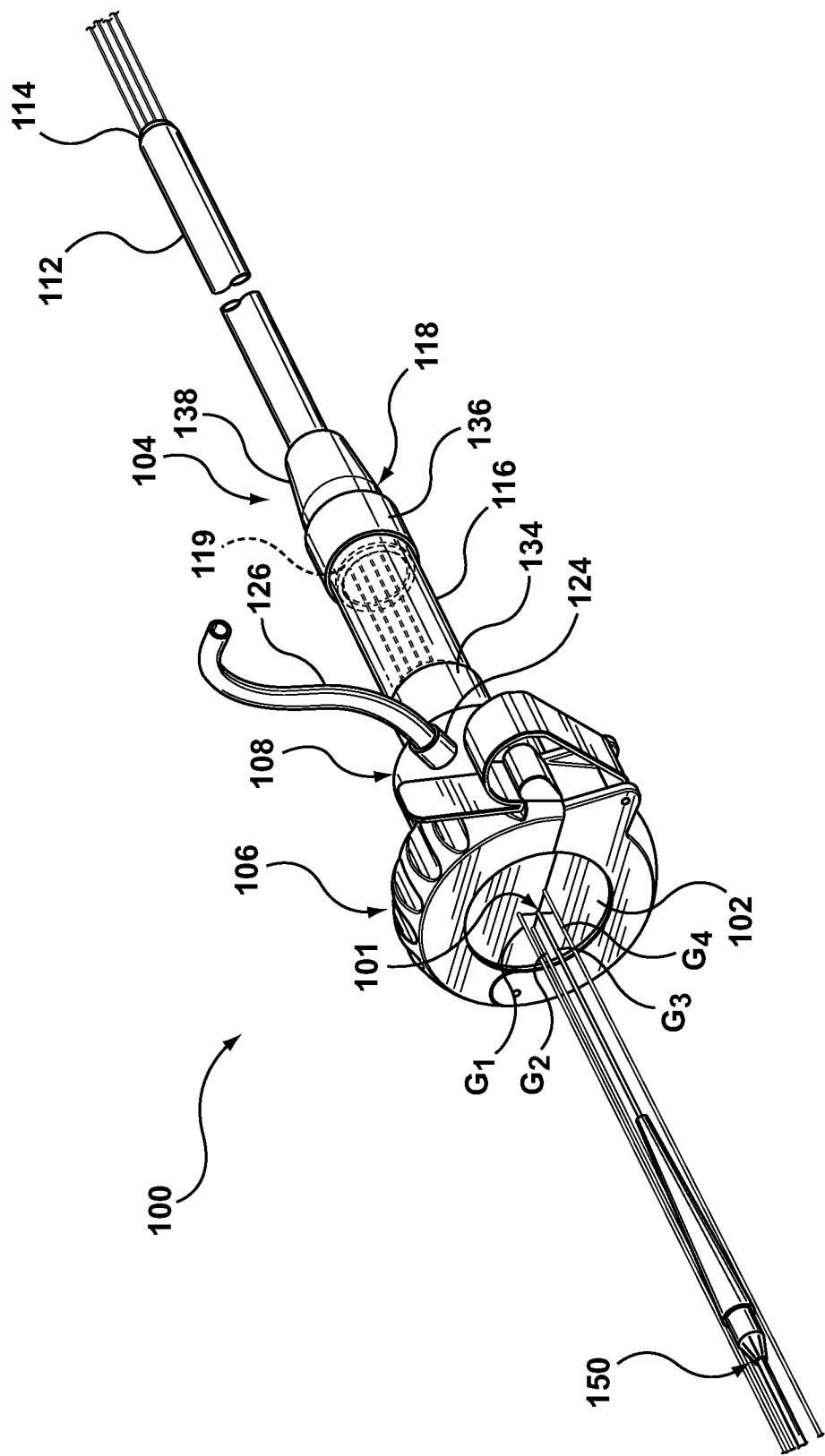
FIG. 1 is a perspective view of a sheath introducer system in accordance with an embodiment hereof having an exchangeable single port valve module affixed therein.
Figure 2:
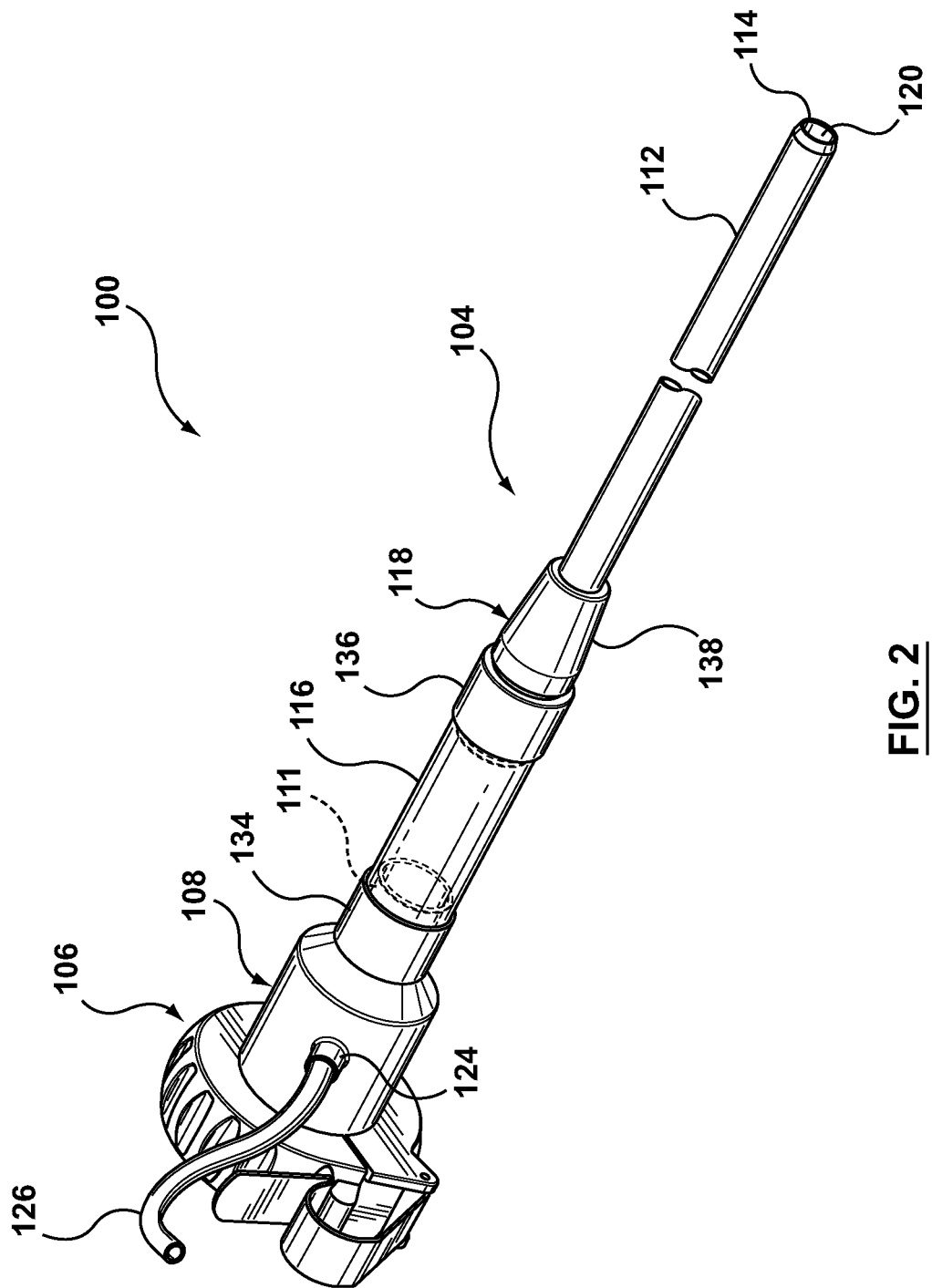
FIG. 2 is an alternate perspective view of the sheath introducer shown in FIG. 1.
Figure 3:
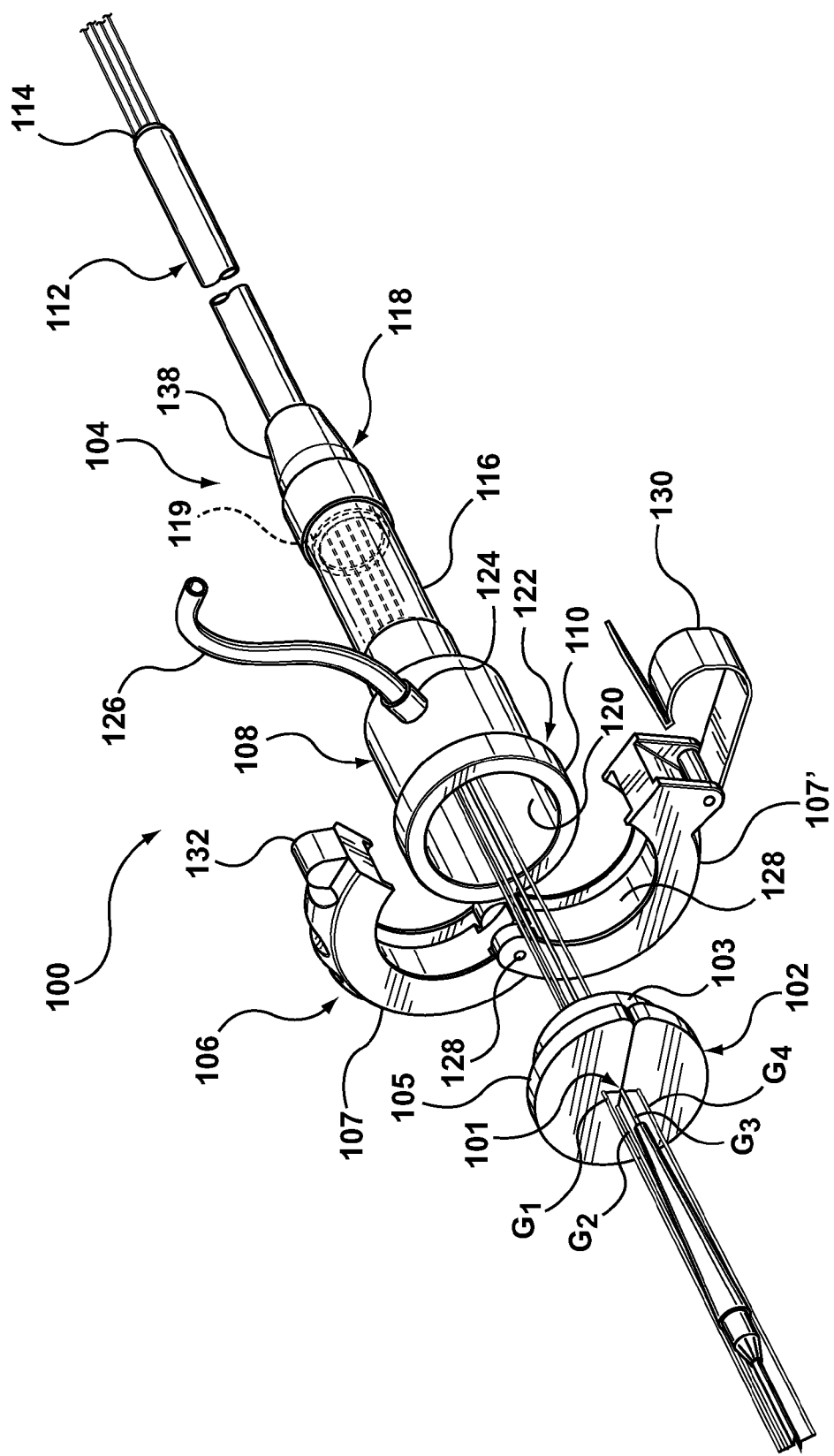
FIG. 3 is a perspective view of the sheath introducer system shown in FIG. 1 during a valve module exchange.

FIGS. 1 and 2 are perspective views of a sheath introducer system 100 in accordance with an embodiment hereof with FIG. 3 depicting sheath introducer system 100 during a valve module exchange. Sheath introducer system 100 maintains a percutaneous opening into the vasculature initially made with another medical device, such as a hypodermic needle or scalpel, and provides an entrance point for a dilator and/or an obturator, as well as for various other interventional devices, such as guidewires and catheters as would be understood by one of ordinary skill in the art. Sheath introducer system 100 includes an exchangeable single port valve module 102, a sheath introducer component 104 and a locking collar 106. In the configuration shown in FIG. 1, the entrance point is a single entry port 101 located within valve module 102 such that when a dilator, obturator, catheter or guidewire is introduced, as will be explained further below, it extends through the length of sheath introducer system 100 and out a distal end 114 thereof into the previously accessed vasculature.

Sheath introducer component 104 has a valve housing 108 defining a proximal end 110 thereof and an elongate tubular sheath or shaft 112 defining distal end 114 of system 100. Valve housing 108 is a sturdy molded component that may in embodiments hereof be formed from a suitable rigid polymeric material such as ABS, HDPE, rigid PVC, polycarbonate, acetal homopolymer, or the like. In embodiments hereof, the material may be opaque or translucent. In another embodiment, a material of valve housing 108 is a transparent material, like PVC, polycarbonate, or the like. Sheath 112 is a tubular structure of a suitable polymeric material and embodiments hereof may be reinforced along its length or a portion of its length by braided stainless steel wire or wire of NiTi, platinum, or a similar high-strength material. In an embodiment, sheath 112 may be reinforced by a helix of wire of NiTi, stainless steel, or similar high strength wire. Valve housing 108 is in fluid communication with sheath 112 by a compressible segment 116 and a rigid tapered component 118, which provides a means of connecting compressible segment 116 to a proximal end of sheath 112. Compressible segment 116 is a tubular structure of an elastomeric material that is configured to be selectively compressed or clamped about an interventional device passing therethrough in such a manner as to permit hemostasis. In an embodiment, compressible segment 116 may be formed of a silicone rubber tubing that is also relatively transparent to allow a clinician to view when hemostasis has been achieved. Together valve housing 108, compressible segment 116, tapered component 118 and sheath 112 define a lumen 120 of sheath introducer component 104 that extends from proximal end 110 of valve housing 108 to distal end 114 of sheath 112. Valve housing 108 includes a side port 124 for coupling with a hose 126 or other flexible tubing that is employed to facilitate perfusion and aspiration of fluids through lumen 120 of sheath introducer component 104.

Proximal end 110 of valve housing 108 has an internal diameter that is sized to receive a corresponding distal segment 103 of valve module 102 therein and has a radially extended flange 122 having an outer diameter that is sized to be substantially equal to an outer diameter of a proximal segment 105 of valve module 102. Valve module 102 is securable to and releasable from proximal end 110 of valve housing 108 by locking collar 106. Locking collar 106, as best shown in FIG. 3, has an internal groove 128 of a width and depth that are sized to snuggly receive both flange 122 of valve housing 108 and an outer circumferential portion of proximal segment 105 of valve module 102 therein when distal segment 103 of valve module 102 is inserted within valve housing proximal end 110 so that valve module proximal segment 105 abuts a proximal surface of valve housing flange 122. In the embodiment shown in FIG. 3, locking collar 106 includes two C-shaped segments 107, 107' coupled at first ends via a hinge 128 and releasably secured together at second ends via interaction between a hinged spring-like clasp 130 and a protrusion 132. When valve module 102 is attached to valve housing 108 by locking collar 106 a fluid tight seal is created to provide hemostasis. More particularly in an embodiment hereof, a width of a base of groove 128 is narrower than a combined width of an outer portion of flange 122 and the outer circumferential portion of proximal segment 105 to create compression of the flange outer portion against the outer circumferential portion of proximal segment 105 to thereby enhance the seal of valve module 102. In another embodiment, a cross-section of groove 128 is trapezoidal with a widest of two parallel sides positioned at an edge of C-shaped segments 107, 107' to be perpendicular to proximal and distal sides of the segments. In various embodiments, segments 107, 107' of locking collar 106 are molded components that are formed from a suitable polymeric rigid material such as ABS, HDPE, rigid PVC, polycarbonate, acetal homopolymer, or the like.

A distal neck portion 111 of valve housing 108 and a proximal portion 119 of tapered component 118 have outer diameters that are sized to create an interference fit with compressible segment 116 and are connected to compressible segment 116 by respective collars 134, 136 that surround the overlapped portions of the joints. The elastomeric material of compressible segment 116 allows it to be stretched over an outer diameter of each of distal neck portion 111 of valve housing 108 and proximal portion 119 of tapered component 118, and the barb features (not shown) extending from each of distal neck portion 111 and proximal portion 119. In an embodiment, collars 134, 136 are made of a heat shrink tubing of polyester, polyolefin, fluoropolymer (FEP, PTFE, or Kynar), or suitable other thermoplastic. In an embodiment, collars 134, 136 are applied as the final components in the assembly of valve housing 108, tapered component 118 and compressible segment 116, wherein the shrinkable collars 134, 136 serve to constrain compressible segment 116 in position mated with distal neck portion 111 and proximal portion 119. In an embodiment, a silicone adhesive (or other elastomeric adhesive may be applied at the respective interfaces between distal neck portion 111 and proximal portion 119 and compressible segment 116. Tapered component 118 in turn has a tapered distal portion 138 with an internal diameter that is sized to receive an outer diameter of sheath 112. Tapered component 118 is a molded component of a suitable rigid polymeric material such as ABS, HDPE, rigid PVC, polycarbonate, acetal homopolymer, or the like. In embodiments hereof, a proximal end of sheath 112 is bonded to tapered component 118 with a suitable adhesive, such as cyanoacrylate, acrylic, or other adhesives, which creates a molecular bond between the two adhered materials. When sheath introducer system 100 is positioned to provide a percutaneous opening into the vasculature, only sheath 112 extends within the accessed vessel and as such an outer diameter and length of sheath 112 are sized to be tracked a distance within the accessed vessel and thereafter function as a pathway into the accessed vessel for subsequently introduced interventional devices. In an embodiment for introducing a 24 F graft delivery system an internal diameter of sheath 112 may be 0.33 inch.

Figure 4:
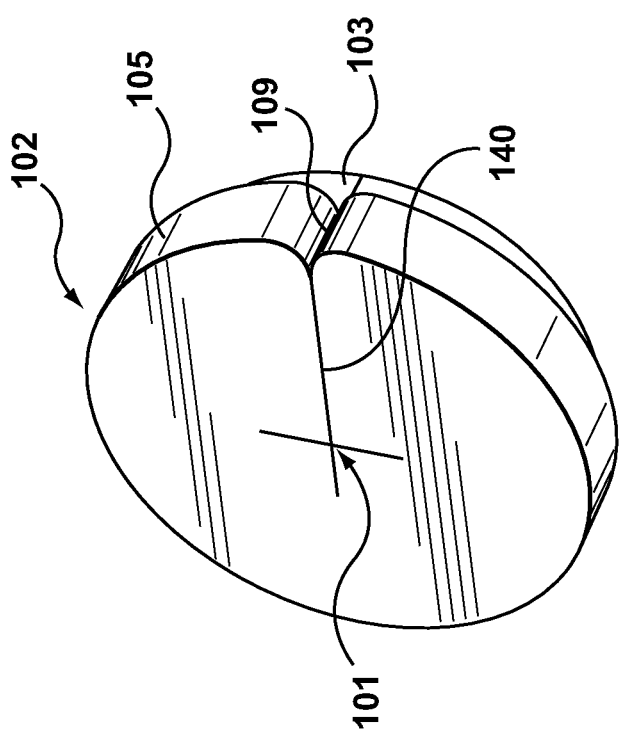
FIG. 4 is a perspective view of the single port exchangeable valve module shown in FIGS. 1 and 3 in accordance with an embodiment hereof.

FIG. 4 is a perspective view of exchangeable single port valve module 102 shown in FIGS. 1 and 3 in accordance with an embodiment hereof. Valve module 102 has a disk-like shape and includes a centrally located entry port 101, as noted above, that extends through the entire thickness of valve module 102. In the embodiment of FIG. 4 entry port 101 is depicted as a cross-shaped slit. In embodiments hereof, valve module 102 is a molded part of an elastomer, such as polyisoprene, silicone rubber, and natural rubber or of a thermoplastic elastomeric material, e.g., injection moldable synthetic rubber compounds, so that an interventional device may be advanced through entry port 101 by compression of the elastomeric material of valve module 102 around a periphery of the interventional device, which ensures hemostasis. In FIGS. 1 and 3 four guidewires $G_1$, $G_2$, $G_3$, $G_4$ are shown extending through entry port 101 and lumen 120 of sheath introducer component 104 to have portions thereof extending proximally and distally of system 100. More particularly with reference to the guidewires interaction with valve module 102, guidewires $G_1$, $G_2$, $G_4$ are shown extending through respective ends of the cross-shaped slit of entry port 101 with guidewire $G_3$ extending through a center of the cross-shaped slit of entry port 101. Valve module 102 also includes a side access slit 140 radially extending through the entire thickness of valve module 102 that provides an interventional device pathway for connecting entry port 101 with a periphery or circumference of valve module 102. Side access slit 140 is utilized for transversely removing interventional devices, such as guidewires $G_1$, $G_2$, $G_3$, $G_4$, from engagement with valve module 102 when an exchange of valve module 102 is to be performed as discussed in more detail below. In the embodiment of FIG. 4, a V-shaped groove or depression 109 in the circumference of proximal segment 105 provides an entry/exit point of side access slit 140 and aids a clinician in locating slit 140 when transverse removal of an interventional device is performed during a valve module exchange.

Figure 7:
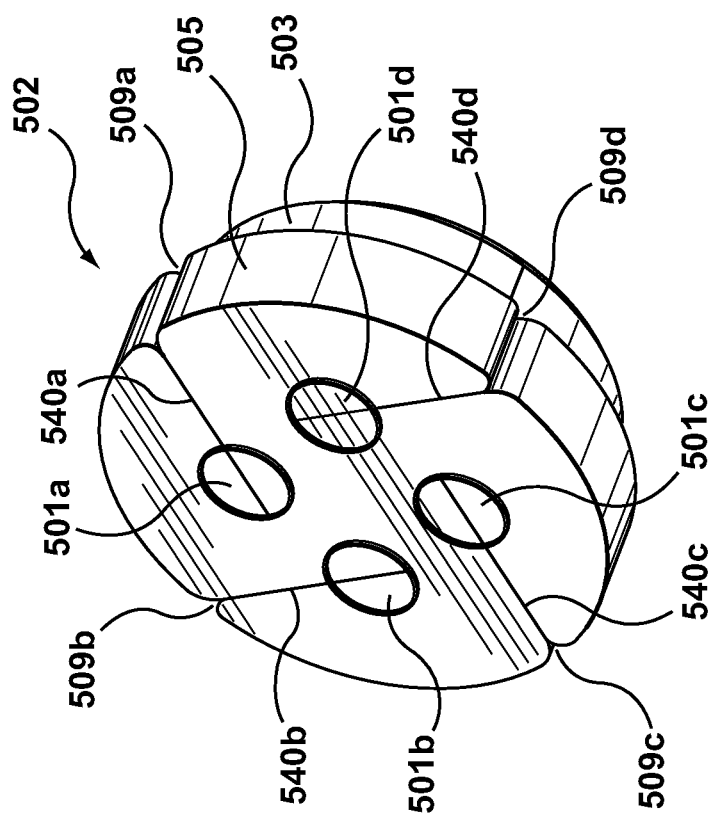
FIG. 7 is a perspective view of the multiple port exchangeable valve module shown in FIGS. 5 and 6 in accordance with an embodiment hereof.
Figure 5:
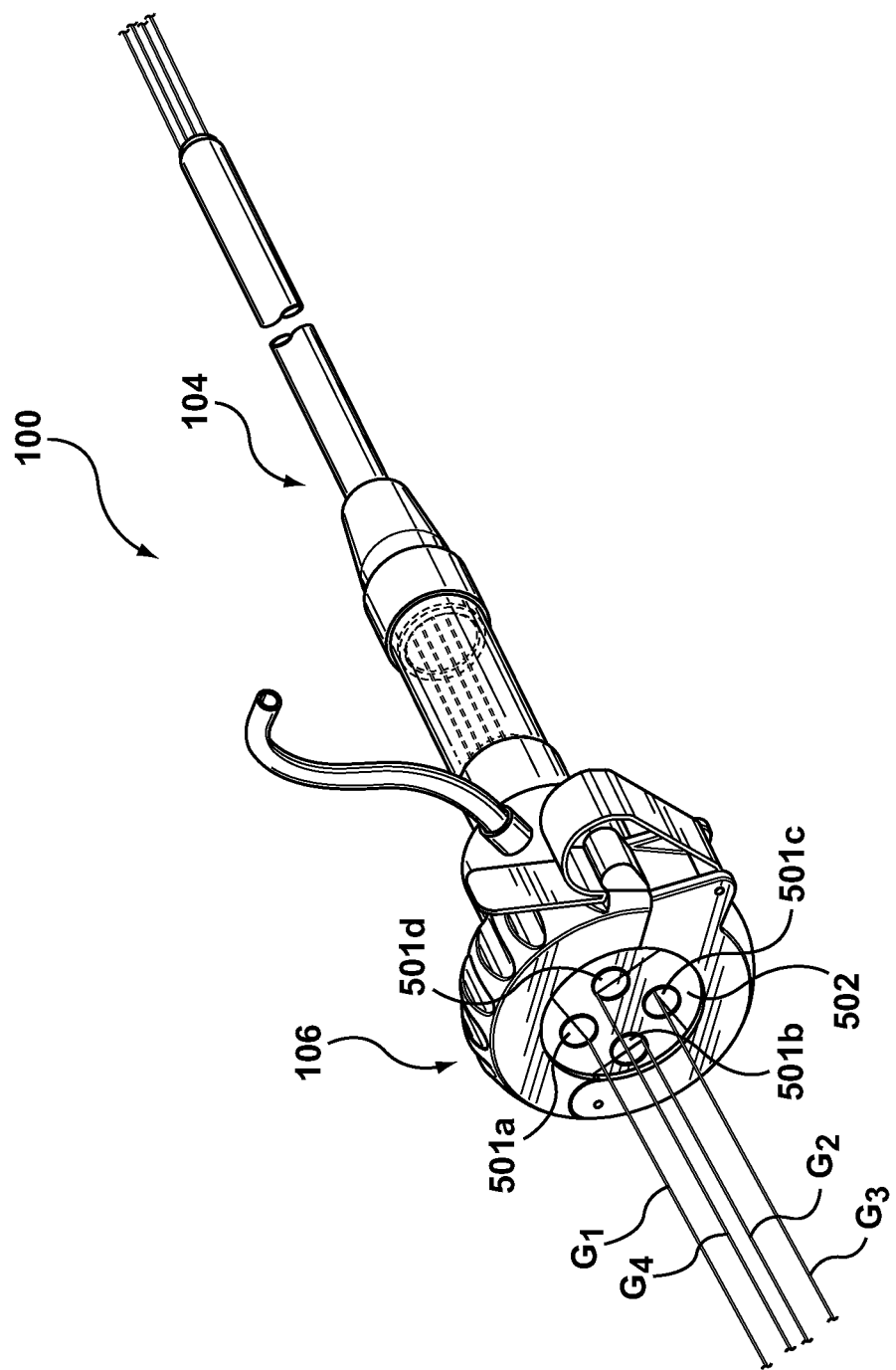
FIG. 5 is a perspective view of the sheath introducer system of FIG. 1 having an exchangeable multiple port valve module affixed therein.
Figure 6:
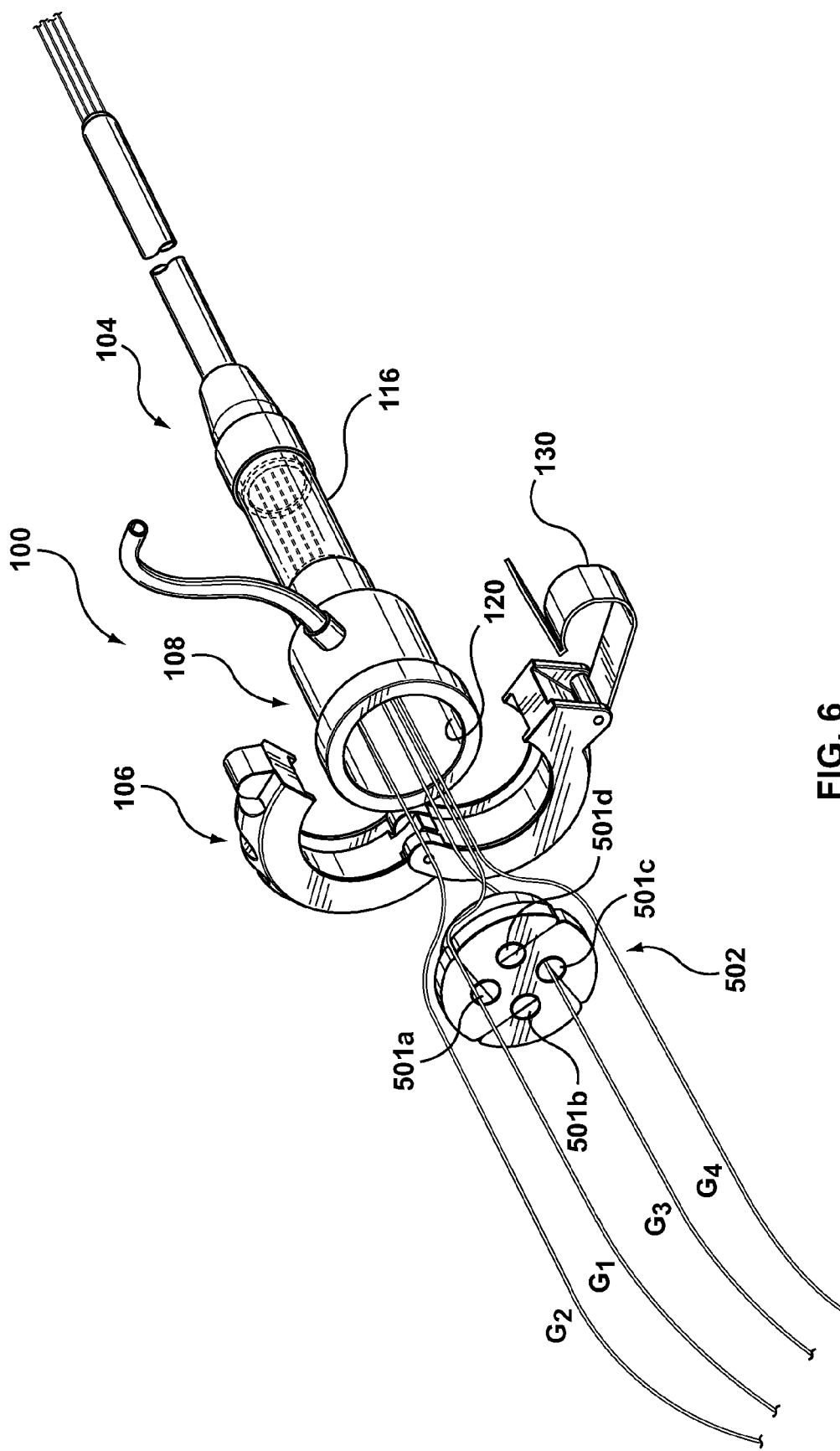
FIG. 6 is a perspective view of the sheath introducer system shown in FIG. 5 during a valve module exchange.

FIG. 5 is a perspective view of sheath introducer system 100 having an exchangeable multiple port valve module 502 attached, with FIG. 6 depicting system 100 during a valve module exchange and FIG. 7 illustrating a perspective view of valve module 502 in accordance with an embodiment hereof. Valve module 502 has a disk-like shape and includes distal and proximal segments 503, 505 that are of the same dimension as distal and proximal segments 103, 105 of valve module 102 described above. Valve module 502 is also a molded part of an elastomeric material and may be made from any of the materials suggested above for valve module 102.

Multiple port valve module 502 is releasably coupled to valve housing 108 by locking collar 106 to provide hemostasis during the simultaneous introduction and manipulation of multiple interventional devices in a similar manner as described with reference to valve module 102. Multiple port valve module 502 differs from valve module 102 in that valve module 502 includes four entry ports 501a, 501b, 501c, 501d for separately receiving four interventional devices. In accordance with other embodiments, a multiple port valve module may include 2, 3 or more than 4 entry ports to suit a particular therapeutic application. In FIGS. 5 and 6 four guidewires $G_1$, $G_2$, $G_3$, $G_4$ are shown extending through or near their respective entry ports 501a, 501b, 501c, 501d and lumen 120 of sheath introducer component 104 to have portions of the guidewires extending proximally and distally of system 100. Each of entry ports 501a, 501b, 501c, 501d includes a respective side access slit 540a, 540b, 540c, 540d that may be used to guide an interventional device, such as one of guidewires $G_1$, $G_2$, $G_3$, $G_4$, to seat within a respective entry port 501a, 501b, 501c, 501d of valve module 502 during a valve module exchange. In the embodiment of FIG. 7, V-shaped grooves or depressions 509a, 509b, 509c, 509d in the circumference of proximal segment 505 provide an entry/exit point of a respective side access slit 540a, 540b, 540c, 540d and aid a clinician in locating the side access slit when transverse coupling of an interventional device to valve module 502 is performed during a valve module exchange.

In accordance with embodiments hereof, sheath introducer system 100 may be used, for instance, to facilitate the treatment of a peri-renal abdominal aortic aneurysm (AAA) with a fenestrated and branched endograft having fixation and sealing proximal to the celiac trunk. A main stent graft includes a fenestration for the superior mesenteric artery (SMA) and two couplings for the renal arteries (RA). The main stent graft is deployed using a delivery system 150 that may be passed through valve module 102, and that has three indwelling guidewires $G_1$, $G_2$, $G_4$ in addition to a main delivery system guidewire $G_3$. When deployment of the main stent graft is complete, the delivery system 150 is withdrawn as shown in FIG. 1, leaving indwelling the main guidewire $G_3$ and the three additional wires $G_1$, $G_2$, $G_4$, which have cannulated the RA couplings and the SMA. Valve module 102 may then be exchanged for valve module 502 to permit sheath introducer system 100 to handle multiple interventional devices to complete the treatment of the AAA while ensuring hemostasis. More particularly, the RA and SMA guidewires $G_1$, $G_2$, $G_4$ will be used to pass successive guiding catheters with the ultimate result of cannulating all three vessels with, for instance, 8 F guiding catheters simultaneously. The guiding catheters will subsequently be used to deploy covered stent grafts that form fluid conduits for connecting the fenestration and couplings of the main stent graft with the branch vessels.

Accordingly, sheath introducer system 100 may be used to introduce a single catheter-based delivery system 150, a distal tip of which is shown in FIG. 1, into the vasculature over guidewire $G_3$ through entry port 101 of valve module 102. Valve module 102 provides hemostasis during use of delivery system 150. In an embodiment catheter-based delivery system 150 may be used to deliver the main stent graft of a therapeutic AAA endograft, as discussed above, and therefore may have a diameter in a range of 18 to 24 F with valve module 102 and the various components of introducer sheath component 104 being sized accordingly. While indwelling, i.e., positioned to extend between sheath introducer system 100 and the treatment site within the aorta, catheter-based delivery system 150 may be used to introduce additional guidewires, such as guidewires $G_1$, $G_2$, $G_4$, to the treatment site such that upon removal of delivery system 150 from the vasculature as many as four guidewires may be left indwelling and extending through entry port 101 of valve module 102 as shown in FIG. 1.

With reference to FIGS. 3 and 6, single port valve module 102 may then be exchanged for multiple port valve module 502. More particularly, clasp 130 of locking collar 106 may be pulled free of or unsnapped from corresponding protrusion 132 to unclamp valve module 102 from valve housing 108 such that valve module 102 may be proximally slid along guidewires $G_1$, $G_2$, $G_3$, $G_4$ until it is generally free of valve housing 108. Guidewires $G_1$, $G_2$, $G_3$, $G_4$ are then disengaged from valve module 102 by being transversely slid out of entry port 101 along side access slit 140. Guidewires $G_1$, $G_2$, $G_3$, $G_4$ are then engaged with valve module 502 by being transversely slid into and through respective side access slits 540a, 540b, 540c, 540d to seat within respective entry ports 501a, 501b, 501c, 501d of the multiple port valve module 502. Valve module 502 is then distally slid along guidewires $G_1$, $G_2$, $G_3$, $G_4$ until distal segment 503 seats within proximal end 110 of valve housing 108 to be secured thereto by locking collar 106. Thereafter valve module 502 in the configuration shown in FIG. 5 provides hemostasis during simultaneous delivery and manipulation of multiple interventional devices, such as the guiding catheters mentioned above each of which may be delivered to the treatment site within the aorta through a respective entry port 501a, 501b, 501c, 501d over a respective guidewires $G_1$, $G_2$, $G_3$, $G_4$. It would be understood by one of ordinary skill in the art that during the exchange of valve module 502 for valve module 102 hemostasis must be maintained for sheath introducer system 100. In an embodiment, hemostasis may be ensured during a valve module exchange by clamping compressible segment 116 of sheath introducer 104 distal of valve housing 108.

A sheath introducer system in accordance with embodiments hereof eliminates threading distal ends of the guidewires through a single port hemostatic valve as would be necessary with hemostatic valves of sheath introducers of the prior art, which can be an arduous task due to the length of a typical guidewire.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A sheath introducer system comprising:
   a sheath introducer defining a lumen therethrough and having a proximal valve housing in fluid communication with a distal tubular sheath, wherein a proximal end of the valve housing defines a proximal opening of the lumen of the sheath introducer;
   an exchangeable valve module coupled to the valve housing to cover the proximal opening of the sheath introducer lumen, the valve module having at least one entry port for receiving an interventional device therethrough, wherein the exchangeable valve module includes a side access slit therethrough that radially extends from the at least one entry port to a periphery of the valve module, whereby the side access slit permits transversely sliding an interventional device from an entry/exit point on the periphery of the valve module into and out of engagement with the at least one entry port of the valve module; and
   a reusable locking collar for releasably securing the valve module to the valve housing of the sheath introducer.

2. The system of claim 1, wherein the valve module includes a plurality of entry ports with each entry port having a corresponding side access slit for receiving a separate interventional device therethrough.

3. The system of claim 1, wherein the proximal end of the valve housing includes a radially extended flange with an outer diameter that is substantially equal to an outer diameter of a proximal segment of the valve module.

4. The system of claim 3, wherein the locking collar is hinged and includes an internal circumferential groove dimensioned to receive the flange of the valve housing and a circumferential portion of the proximal segment of the valve module when the locking collar is used to secure the valve module to the valve housing.

5. The system of claim 1, wherein the sheath introducer further comprises a tubular segment of a compressible material that is disposed between the valve housing and the tubular sheath, wherein the tubular segment is clampable to an interventional device extending therethrough to provide hemostasis during a valve module exchange.

6. A sheath introducer system comprising:
   a sheath introducer defining a lumen that extends through a valve housing that forms a proximal portion of the sheath introducer and a tubular sheath that forms a distal portion of the sheath introducer, wherein a proximal end of the valve housing defines a proximal opening of the lumen of the sheath introducer;
   an exchangeable valve module dimensioned such that a distal segment thereof is insertable within the lumen of the valve housing and a proximal segment thereof is abuttable against a proximal surface of the valve housing, the valve module having at least one entry port for receiving an interventional device therethrough; and
   a locking collar for releasably securing the valve module to the valve housing of the sheath introducer, wherein when the valve module is secured to the valve housing the proximal segment thereof abuts the proximal surface of the valve housing.

7. The system of claim 6, wherein the exchangeable valve module includes a side access slit extending therethrough that connects the at least one entry port with a periphery of the valve module, whereby the side access slit permits transversely sliding an interventional device from the periphery of the valve module into and out of engagement with the at least one entry port of the valve module.

8. The system of claim 7, wherein the valve module includes a plurality of entry ports with each entry port having a corresponding side access slit for receiving a separate interventional device therethrough.

9. The system of claim 6, wherein the proximal end of the valve housing includes a radially extended flange with an outer diameter that is substantially equal to an outer diameter of the proximal segment of the valve module, wherein the radially extended flange defines the proximal surface of the proximal portion.

10. The system of claim 9, wherein the locking collar is hinged and includes an internal circumferential groove dimensioned to receive the flange of the valve housing and a circumferential portion of the proximal segment of the valve module when the locking collar is used to secure the valve module to the valve housing.

11. The system of claim 6, wherein the sheath introducer further comprises a tubular segment of a compressible material that is disposed between the valve housing and the tubular sheath, wherein the tubular segment is clampable to an interventional device extending therethrough to provide hemostasis during a valve module exchange.

12. A sheath introducer kit comprising:
   a sheath introducer defining a lumen that extends therethrough and having a proximal valve housing in fluid communication with a distal tubular sheath, wherein a proximal end of the valve housing includes a radially extended flange;
   a first valve module dimensioned to be coupled with the valve housing, the first valve module having at least one entry port for receiving an interventional device therethrough, the first valve module having a proximal segment with an outer diameter that is substantially equal to an outer diameter of the radially extended flange of the valve housing, wherein when the first valve module is secured to the valve housing the proximal segment thereof abuts a proximal surface of the radially extended flange of the valve housing;
   a second valve module dimensioned to be coupled with the valve housing, the second valve module having a plurality of entry ports with each entry port for receiving a separate interventional device therethrough, the second valve module having a proximal segment with an outer diameter that is substantially equal to the outer diameter of the radially extended flange of the valve housing, wherein when the second valve module is secured to the valve housing the proximal segment thereof abuts a proximal surface of the radially extended flange of the valve housing; and a reusable locking collar for interchangeably securing the first valve module or the second valve module to the valve housing of the sheath introducer, wherein the locking collar is hinged and includes an internal circumferential groove dimensioned to receive the radially extended flange of the valve housing and a circumferential portion of one of the proximal segments of the first and second valve modules when the locking collar is used to secure one of the first and second valve modules to the valve housing.

13. The kit of claim 12, wherein the first valve module includes a side access slit extending therethrough that connects the at least one entry port thereof with a periphery of the first valve module, whereby the side access slit permits transversely sliding an interventional device from the periphery of the first valve module into and out of engagement with the at least one entry port of the first valve module.

14. The kit of claim 12, wherein each of the entry ports of the second valve module includes a side access slit that connects the respective entry port with a periphery of the second valve module, whereby the side access slit permits transversely sliding an interventional device from the periphery of the second valve module into and out of engagement with the respective entry port.

* * * * *